(12) United States Patent
Basu et al.

(10) Patent No.: US 8,377,033 B2
(45) Date of Patent: Feb. 19, 2013

(54) METHODS OF MODIFYING MYOCARDIAL INFARCTION EXPANSION

(75) Inventors: Shubhayu Basu, Cleveland, OH (US); Randolf von Oepen, Los Altos, CA (US); Eugene Michal, San Francisco, CA (US); Florian Ludwig, Ebikon (CH)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 156 days.

(21) Appl. No.: 12/877,820

(22) Filed: Sep. 8, 2010

(65) Prior Publication Data
US 2012/0059355 A1    Mar. 8, 2012

(51) Int. Cl.
*A61M 25/00* (2006.01)
(52) U.S. Cl. .......................... 604/511; 600/37
(58) Field of Classification Search ............... 604/507, 604/508, 511; 600/37
See application file for complete search history.

(56) References Cited

U.S. PATENT DOCUMENTS

| 6,702,744 | B2 | 3/2004 | Mandrusov et al. |
| 7,762,958 | B1 | 7/2010 | Webler |
| 2002/0188170 | A1* | 12/2002 | Santamore et al. ............. 600/37 |
| 2005/0271631 | A1* | 12/2005 | Lee et al. ...................... 424/93.7 |
| 2007/0218118 | A1 | 9/2007 | Michal et al. |
| 2008/0025943 | A1 | 1/2008 | Michal et al. |
| 2008/0058759 | A1* | 3/2008 | Makower et al. ............. 604/509 |
| 2008/0119385 | A1 | 5/2008 | Michal et al. |

FOREIGN PATENT DOCUMENTS
WO    WO 2008/089452    7/2008

* cited by examiner

*Primary Examiner* — Emily Schmidt
(74) *Attorney, Agent, or Firm* — Blakely Sokoloff Taylor & Zafman LLP

(57) ABSTRACT

A reinforcement region is formed within the myocardium by introducing a delivery device through a vessel wall to a treatment site within a myocardium. A biomaterial is then delivered to the treatment site as the delivery device is withdrawn from the treatment site to form the reinforcement regions. Formation of the reinforcement region may further include introducing a delivery device through a vessel wall to a region within a myocardium such that the delivery device is positioned within the myocardium substantially parallel to a wall of the myocardium. A biomaterial may be delivered into a space formed within the region by the delivery device. The reinforcement region may be formed around an infarct tissue region of a myocardium to reinforce the damaged tissue.

21 Claims, 6 Drawing Sheets

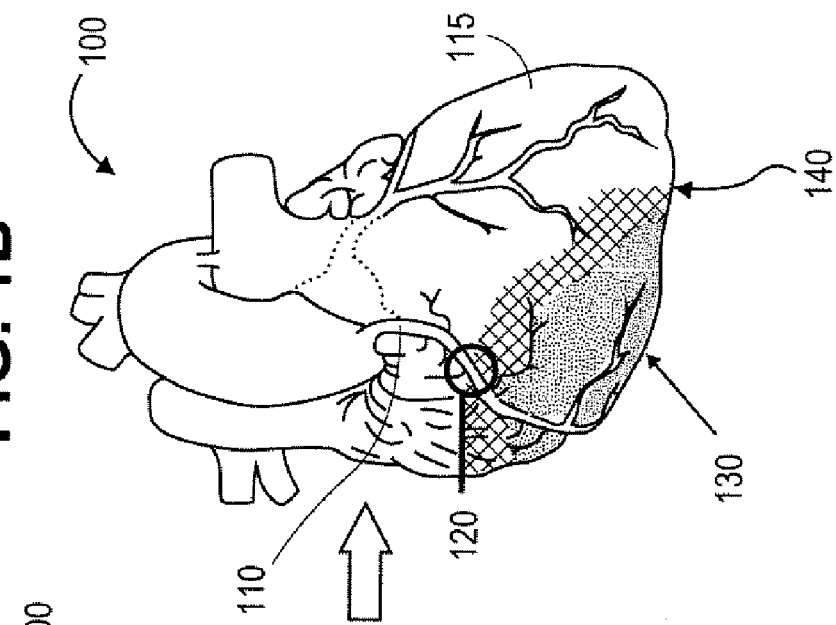
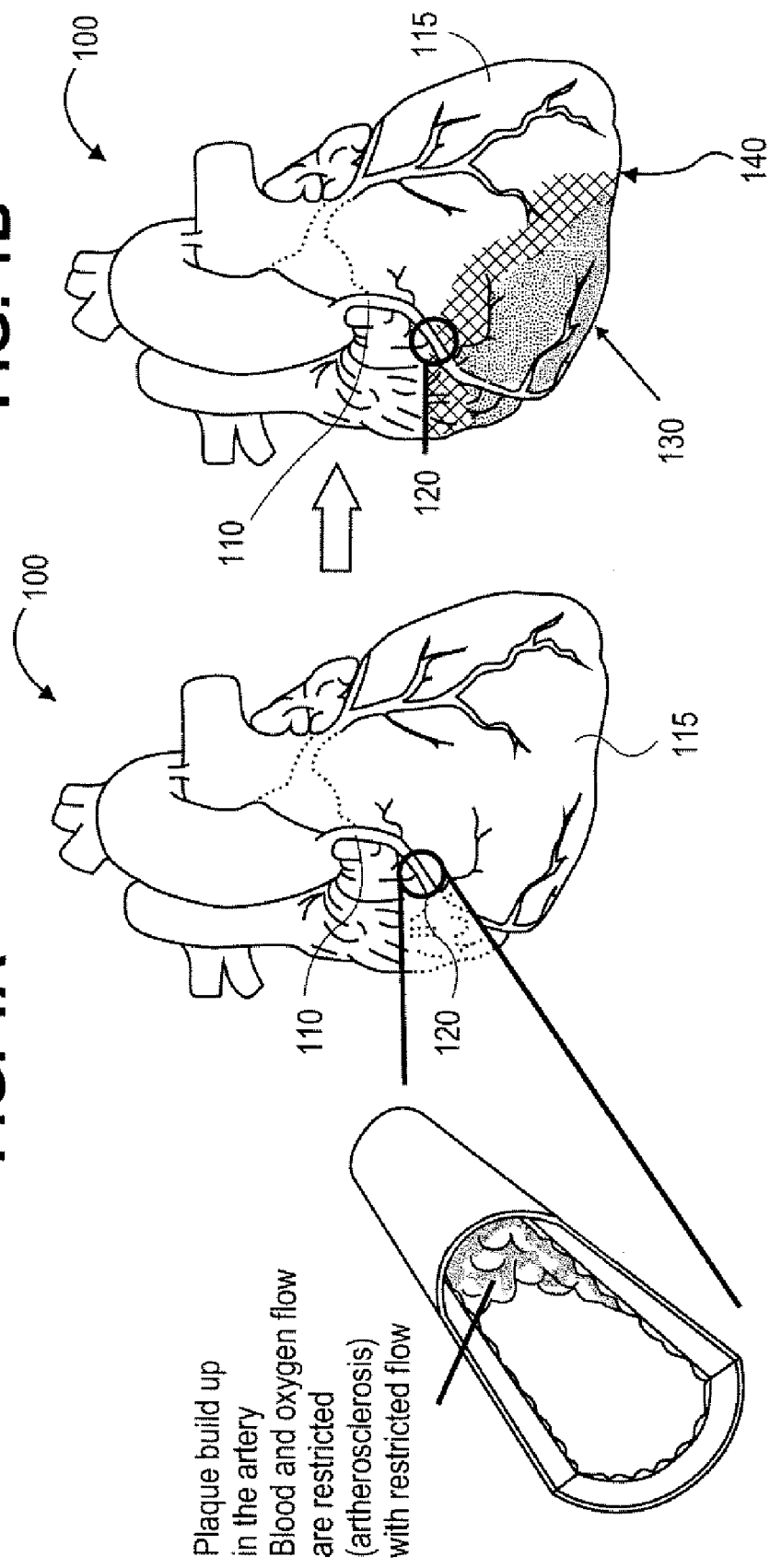

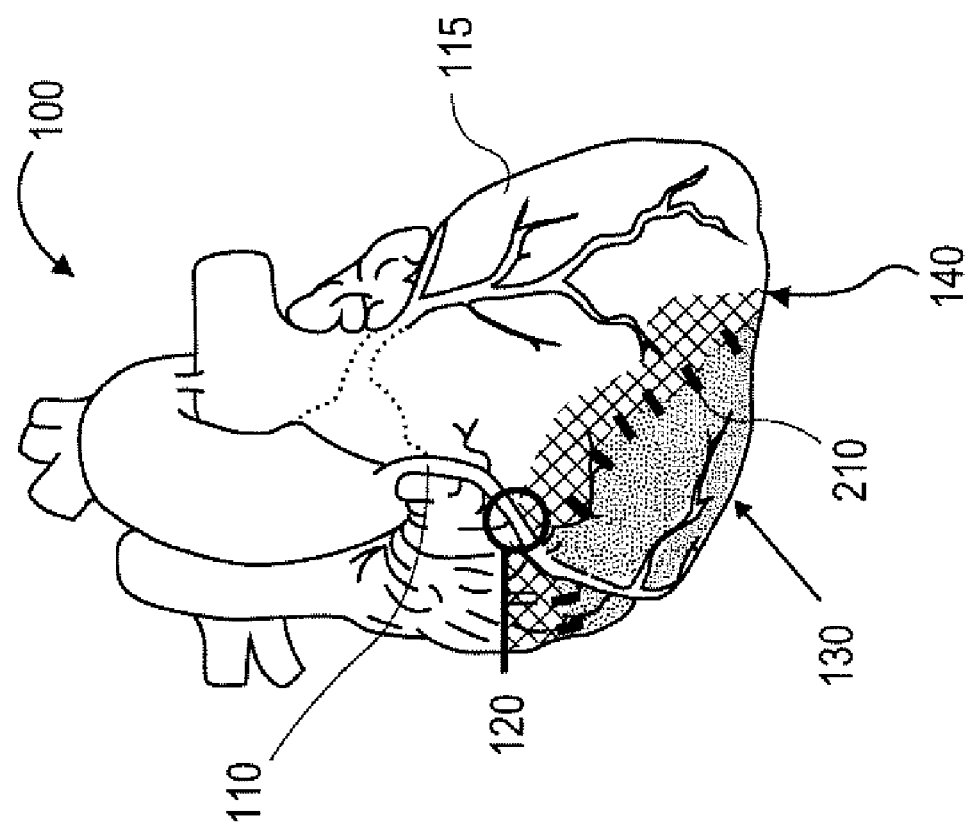

METHODS OF MODIFYING MYOCARDIAL INFARCTION EXPANSION

FIELD

Post-myocardial infarction treatments and compositions.

BACKGROUND

Ischemic heart disease typically results from an imbalance between the myocardial blood flow and the metabolic demand of the myocardium. Progressive atherosclerosis with increasing occlusion of coronary arteries leads to a reduction in coronary blood flow. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one faun of heart disease that often results from the sudden lack of supply of oxygen and other nutrients. The lack of blood supply is a result of the closure of the coronary artery (or any other artery feeding the heart) that nourishes a particular part of the myocardium (i.e., heart muscle). For example, the coronary artery may contain a blockage. The cause of this event is generally attributed to arteriosclerosis in coronary vessels, the "hardening of the arteries." MI may also be the result of minor blockages where, for example, there is a rupture of cholesterol plaque resulting in blood clotting within the artery. Thus, the flow of blood is blocked and downstream cellular damage occurs. As a result of this insult to the heart tissue, scar tissue tends to naturally form.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and therapeutic agent application procedures, are known for reopening blocked arties. An example of a mechanical procedure includes balloon angioplasty with stenting, while an example of a therapeutic agent application includes the administration of a thrombolytic agent, such as urokinase. Such procedures do not, however, treat actual tissue damage to the heart. Other systemic drugs, such as ACE-inhibitors and Beta-blockers, may be effective in reducing cardiac load post-MI, although a significant portion of the population that experiences a major MI ultimately develop heart failure.

An important component in the progression to heart failure is remodeling of the heart due to mismatched mechanical forces between the infarcted region and the healthy tissue resulting in uneven stress and strain distribution in the left ventricle (LV). Once an MI occurs, remodeling of the heart begins. The principle components of the remodeling event include myocyte death, edema and inflammation, followed by fibroblast infiltration and collagen deposition, and finally scar formation from extra-cellular matrix (ECM) deposition. The principle component of the scar is collagen which is non-contractile and causes strain on the heart with each beat. Non-contractility causes poor pump performance as seen by low ejection fraction (EF) and akinetic or diskinetic local wall motion. Low EF leads to high residual blood volume in the ventricle, causes additional wall stress and leads to eventual infarct expansion via scar stretching and thinning and border-zone cell apoptosis. In addition, the remote-zone thickens as a result of higher stress which impairs systolic pumping while the infarct region experiences significant thinning because mature myocytes of an adult are not regenerated. Myocyte loss is a major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes also correlate with physiological changes that result in increase in blood pressure and worsening systolic and diastolic performance.

SUMMARY OF INVENTION

A reinforcement region can be formed within the myocardium by introducing a delivery device through a vessel wall to a treatment site within a myocardium. The treatment site may be an infarct tissue or a tissue within a border region adjacent to the infarct tissue. A biomaterial is then delivered to the treatment site as the delivery device is withdrawn from the treatment site to form the reinforcement regions. Formation of the reinforcement region may further include introducing a delivery device through a vessel wall to a region within a myocardium such that the delivery device is positioned within the myocardium substantially parallel to a wall of the myocardium. A biomaterial may be delivered into a space formed within the region by the delivery device. The reinforcement region may be formed around an infarct tissue region of a myocardium to reinforce the damaged tissue.

The biomaterial may include a single-component gel system or a two-component gel system which forms a tissue reinforcing bioscaffolding when injected into the myocardium. The bioscaffolding can be formed by a single biomaterial or a mixture of biomaterial components of different two-component gelation systems. In some embodiments, a bioscaffolding can be foamed by mixing at least two different components (which do not gel upon mixing) of at least two different two-component gelation systems to form a first mixture and by mixing at least two different components (other than the components that make up the first mixture and which do not gel upon mixing) of the at least two different two-component gelation systems to form a second mixture. A treatment agent can be added to either the first mixture or the second mixture. The first mixture can then be co-injected with the second mixture to form a bioscaffolding in an infarct region for treatment thereof.

The biomaterials can be injected and/or co-injected with a single-lumen or dual-lumen delivery device, which can include, but is not limited to, a catheter, a dual syringe, a dual-needle transvascular wall injection device and the like.

BRIEF DESCRIPTION OF DRAWINGS

FIGS. 1A-1B illustrate the progression of heart damage once the build-up of plaque in an artery induces an infarct to occur.

FIG. 2 illustrates a heart once infarct has occurred having reinforcement regions.

DETAILED DESCRIPTION

Figures 3A, 3B:
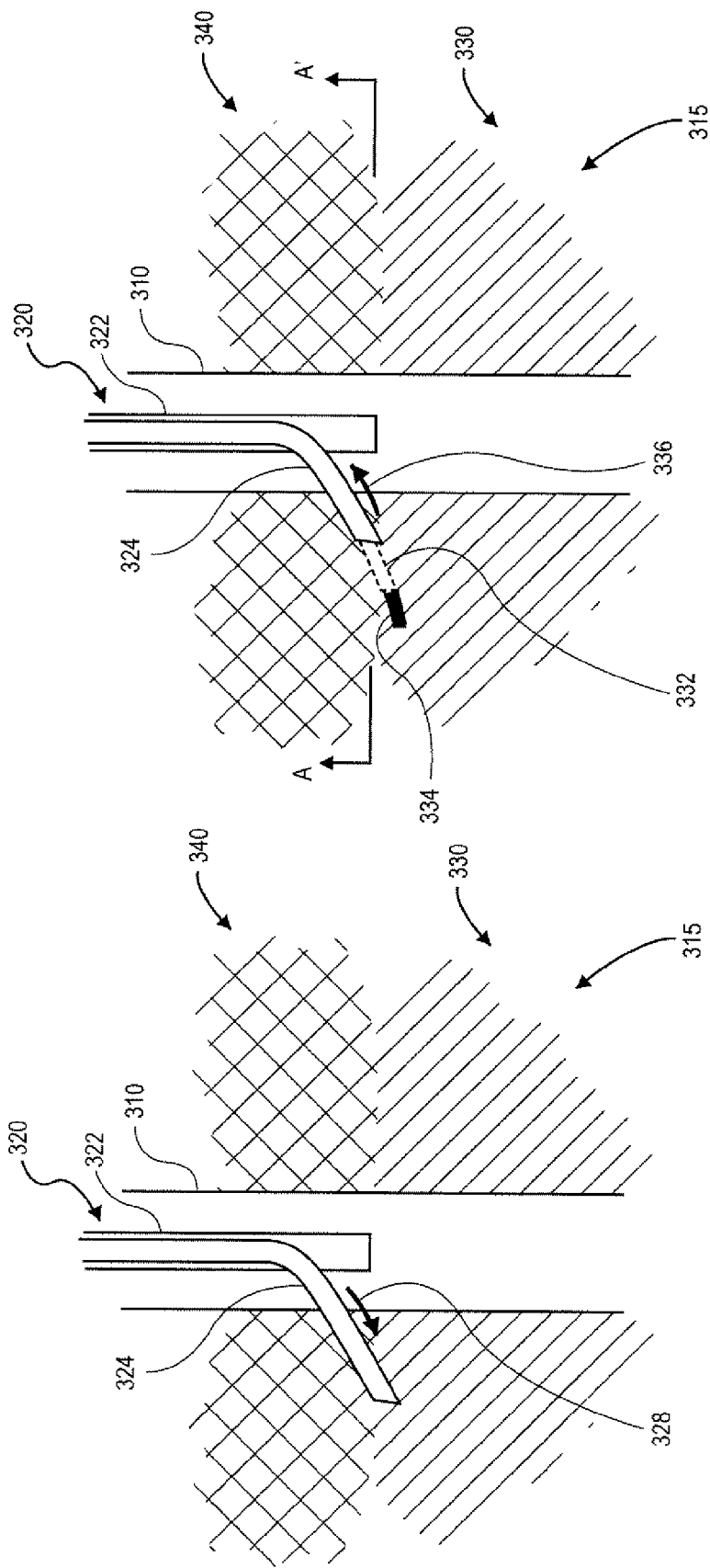
FIGS. 3A-3B illustrate a technique for forming reinforcement regions in a myocardium of a heart.

FIGS. 1A-1B illustrate the progression of heart damage once the build-up of plaque induces an infarct to occur. Blood vessels such as coronary artery 110 are shown exposed around myocardium 115 of heart 100 and beneath the pericardium (not shown). FIG. 1A illustrates a site of blockage 120 and the resulting restricted blood flow that can occur from any of the previously indicated causes. FIG. 1B illustrates the extensive damage to the left ventricle that can be a result of the lack of oxygen and nutrient flow to the left ventricle of heart 100. FIG. 1B illustrates the two areas of an infarct region of myocardium 115. The infarct region has (1) "necrotic zone" 130 which is a region of significant necrosis/apoptosis tissue and (2) "border zone" 140 that includes a large concentration of apoptotic and necrotic tissue as well as viable tissue. In FIG. 1B, border zone 140 is shown surrounding necrotic zone 130. In border zone 140, the cells exist in an oxygen-deprived state due to blockage 120 of coronary artery 110. The region of the heart beyond border zone 140 is the "remote zone" which is remote of the infarct region and of the damage and generate connotes healthy myocardial tissue. Following a MI, the scarred tissue within necrotic zone 130 provides an area of mechanical mismatch with the viable tissue of border zone 140 and/or the remote zone. The scarred tissue dilates resulting in further damage to myocardium 115.

FIG. 2 illustrates reinforcement regions in the myocardium to minimize dilation of the scarred tissue. In particular, reinforcement regions 210 are formed within myocardium 115 along necrotic zone 130 and border zone 140 to reinforce and minimize dilation of the scar tissue. Although not shown, reinforcement regions may further be formed within necrotic zone 130 where additional reinforcement of the scarred tissue is desired.

Reinforcement regions 210 are made of a biomaterial which forms a tissue reinforcing bioscaffolding when injected into myocardium 115. It is contemplated that the biomaterial may further elicit an internal immune response within myocardium 115 which will create a capsule of extra cellular matrix around the material to further stiffen the area and provide added reinforcement. As will be described in more detail below, representative biomaterials may include, but are not limited to, one-component gel systems or two-component gel systems. The biomaterials may be used alone or in conjunction with treatment agents. Representative treatment agents may include, but are not limited to, small molecule drugs, oligonucleotides, peptides and proteins which can inhibit the negative remodeling response, stimulate angiogenesis or regeneration of cardiac tissue.

As can be seen from FIG. 2, reinforcement regions 210 are formed along necrotic zone 130 and border zone 140. Reinforcement regions 210 are positioned along this mismatched region to foul) internal "stitches" which essentially suture necrotic zone 130 and border zone 140 together. "Stitching" tissues within these regions together with the biomaterial reinforces the mismatched tissues by preventing scar expansion and remodeling. In some embodiments, reinforcement regions 210 are formed within portions of necrotic zone 130 and border zone 140. In other embodiments, reinforcement regions 210 are formed within necrotic zone 130, border zone 140 and/or a remote zone remote of the infarct region and of the damage. Representatively, in some cases, the vasculature within necrotic zone 130 may be damaged to the extent that it is not accessible to a delivery device. As a result, the delivery device cannot deliver biomaterials to necrotic zone 130. In such cases, it may only be possible to advance the delivery device as far as border zone 140 such that the biomaterial can only be injected into border zone 140 and/or the remote zone.

FIGS. 3A-3B illustrate a technique for forming reinforcement regions in a myocardium of a heart. Delivery device 320 is advanced through vessel 310 to a desired treatment site. Delivery device 320 may be any delivery device suitable for delivering a biomaterial to myocardium 315 as described herein. Exemplary delivery devices are described in reference to FIG. 5 and FIG. 6 discussed in further detail below. Delivery device 320 generally includes delivery cannula 322 and needle 324. In some embodiments, delivery device 320 may further include a guidewire cannula to facilitate positioning of needle 324 within a desired region of myocardium 315. Needle 324 (and in some cases a guidewire cannula) is positioned within delivery cannula 322. Once a desired treatment site is reached, needle 324 is advanced in a direction of arrow 328 through an opening of delivery cannula 322. Needle 324 pierces through a wall of vessel 310 and into myocardium 315. In some embodiments, needle 324 is advanced through necrotic zone 330 and/or border zone 340.

To form reinforcement region 334 illustrated in FIG. 3B, needle 324 is retracted in a direction of arrow 336 to form space 332 within myocardium 315. As needle 324 is retracted, the biomaterial is simultaneously ejected from needle 324 such that it fills in space 332 to fowl reinforcement region 334. In this aspect, the dimensions of reinforcement region 334 are determined by a size of needle 324 and the amount and type of biomaterial injected from needle 324. For example, a length of reinforcement region 334 will depend on the amount of biomaterial injected into space 332 as needle 324 is withdrawn. In some embodiments, reinforcement region 334 may be from about 1 centimeter to about 4 centimeters long. For example, the length of reinforcement region may be 0.5 centimeters to 4.5 centimeters or from 1.5 centimeters to 3.5 centimeters. A width of space 332 is determined by a diameter of needle 324 thus a narrower needle will create a narrow space 332 and in turn a narrower reinforcement region 334 than that of a wider needle. In addition, some biomaterials diffuse more than others within the myocardial tissue thereby creating a wider reinforcement region 334 than a biomaterial which diffuses less.

Figure 4:
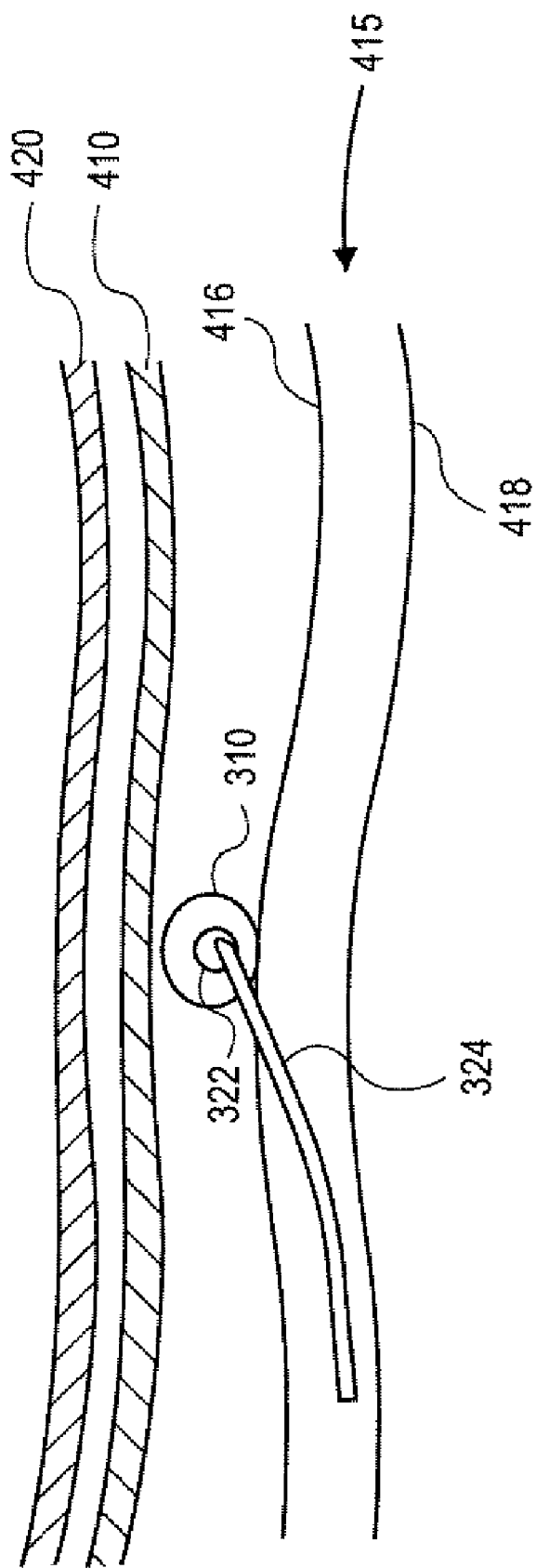
FIG. 4 illustrates a cross section along line A-A' of FIG. 3B.

In some embodiments, needle 324 is inserted into myocardium 415 substantially parallel to walls of myocardium 415 as illustrated in FIG. 4 to form reinforcement region 334. FIG. 4 illustrates a cross section along line A-A' of FIG. 3B. Vessel 310 is positioned between pericardium 420 and myocardium 415. Fat layer 410 is further shown in FIG. 4 overlying vessel 310. Myocardium 415 includes outer walls 416 and 418. Needle 324 is positioned within myocardium 415 such that it is substantially parallel to outer walls 416 and 418. Since needle 324 is positioned in this manner, the risk of damage to other tissues or organs adjacent to the treatment site is minimized. In particular, needle 324 is confined to an area within myocardium and does not protrude beyond the myocardial tissue. To facilitate positioning of needle 324 in this manner, needle 324 may be curved and/or self-orienting to ensure needle 324 is advanced through myocardium 415 between walls 416 and 418.

Biomaterials

In some embodiments, the biomaterial may form a bioscaffolding when injected into the myocardial tissue. The bioscaffolding is formed of a single biomaterial component or two biomaterial components which, when injected into the myocardial tissue, form the reinforcing bioscaffolding or reinforcement region to reinforce the desired region. In some embodiments, the bioscaffolding may be a gel which forms in the tissue upon injection of the biomaterial component. In this aspect, the bioscaffolding may be a single-component gel (made of a single biomaterial component) or a two-component gel (made of two biomaterial components). As "bioscaffolding," the biomaterial, when disposed in myocardial tissue, acts to support the myocardial tissue by making the myocardial tissue at that location less compliant, e.g., reducing the tissue's ability to expand. Representative biomaterials for a single component gel may include, for example, an acrylate agent that is biocompatible, self-assembled peptides, silk-elastin block co-polymers, sodium hyaluronate or its derivatives (e.g. benzyl ester, thiolated, etc). Representative biomaterials for a two-component gel may include, for example, fibrin glues (e.g., two components comprising fibrinogen and thrombin), self-assembled peptides or alginate constructs. Other representative biomaterials suitable for single-component or two-component gels are described below.

Each component of the two-component gel system may be co-injected to an infarct region by a dual-lumen delivery device. Examples of dual-lumen delivery devices include, but are not limited to, a dual syringe, dual-needle left-ventricle injection devices, dual-needle transvascular wall injection devices and the like.

In some embodiments, at least one cell type may be co-injected with at least one component of the two-component gel system to the desired region (e.g. necrotic zone and border zone). In some embodiments, the cells may be mixed with at least one component of the two-component gel system before the two-components are co-injected to the infarct region. Examples of cell types, include, but are not limited to, localized cardiac progenitor cells, mesenchymal stem cells, bone marrow derived mononuclear cells, adipose stem cells, embryonic stem cells, umbilical cord blood derived stem cells, smooth muscle cells or skeletal myoblasts.

In some applications, the two-component gel system includes a fibrin glue. Fibrin glue consists of two main components, fibrinogen and thrombin. Fibrinogen is a plasma glycoprotein of about 340 kiloDaltons (kDa) in its endogenous state. Fibrinogen is a symmetrical dimer comprised of six paired polypeptide chains, alpha, beta and gamma chains. On the alpha and beta chains, there is a small peptide sequence called a fibrinopeptide which prevents fibrinogen from spontaneously forming polymers with itself. In some embodiments, fibrinogen is modified with proteins. Thrombin is a coagulation protein. When combined in equal volumes, thrombin converts the fibrinogen to fibrin by enzymatic action at a rate determined by the concentration of thrombin. The result is a biocompatible gel which gelates when combined at the desired region. Fibrin glue can undergo gelation between about 5 to about 60 seconds. Examples of other fibrin glue-like systems include, but are not limited to, Tisseel™ (Baxter), Beriplast P™ (Aventis Behring), Biocol® (LFB, France), Crosseal™ (Omrix Biopharmaceuticals, Ltd.), Hemaseel HMN® (Haemacure Corp.), Bolheal (Kaketsuken Pharma, Japan) and CoStasis® (Angiotech Pharmaceuticals).

In some applications, the single-component or two-component gel system includes self-assembled peptides. Self-assembled peptides generally include repeat sequences of alternating hydrophobic and hydrophilic amino acid chains. The hydrophilic amino acids are generally charge-bearing and can be anionic, cationic or both. Examples of cationic amino acids are lysine and arginine. Examples of anionic amino acids are aspartic acid and glutamic acid. Examples of hydrophobic amino acids are alanine, valine, leucine, isoleucine or phenylalanine. Self-assembled peptides can range from 8 to 40 amino acids in length and can assemble into nanoscale fibers under conditions of physiological pH and osmolarity. In sufficient concentration and over time, the fibers can assemble into an interconnected structure that appears macroscopically as a gel. Self-assembled peptides typically undergo gelation between several minutes to several hours. Examples of self-assembled peptides include, but are not limited to: AcN-RARADADARARADADA-CNH$_2$ (RAD 16-H) wherein R is arginine, A is alanine, D is aspartic acid, and Ac indicates acetylation; VKVKVKVKV-PP-TKVKVKVKV-NH$_2$ (MAX-1) wherein V is valine, K is lysine and P is proline; and AcN-AEAEAKAKAEAE-AKAK-CNH$_2$ wherein A is alanine, K is lysine and E is glutamic acid (EAK 16-1). Self-assembled peptides show good cytocompatibility, as represented by cell adhesion, cell migration and proliferation.

In some applications, the two-component gel system is an alginate construct system. One component may be an alginate conjugate (or alginate alone) which can include alginate and a protein constituent. The second component may be a salt. Examples of alginate conjugates can include, but are not limited to, alginate-collagen, alginate-laminin, alginate-elastin, alginate-collagen-laminin and alginate-hyaluronic acid in which the collagen, laminin, elastin, collagen-laminin or hyaluronic acid is covalently bonded (or not bonded) to alginate. Examples of salts which can be used to gel the alginate constructs include, but are not limited to, calcium chloride (CaCl$_2$), barium chloride (BaCl$_2$) or strontium chloride (SrCl$_2$). When the components are combined, for example, alginate-collagen and calcium chloride, the resulting gel has a storage modulus of approximately 1 kiloPascal.

In one embodiment, the alginate construct is alginate-gelatin. The molecular weight of the gelatin may be in the approximate range of 5 kDa to 100 kDa. The relatively low molecular weight of gelatin offers processing advantages in that it is more soluble and has lower viscosity than hydrogels of higher molecular weight. Another advantage of gelatin is that it contains from 1 to 4 RGD (arginine-glycine-aspartic acid peptide sequence) sites per molecule. RGD is a common cell adhesion ligand and would increase the retention of cells within the border zone and/or necrotic zone where the bioscaffolding is formed. The cells retained by the RGD sites may be cells co-injected with the bioscaffolding components or dispersed throughout a component of the system.

The gelatin may be a porcine gelatin or a recombinant human gelatin. The porcine gelatin is a hydrolyzed type I collagen extracted from porcine skin. In one embodiment, the molecular weight of the porcine gelatin is approximately 20 kDa. The human gelatin is produced by bacteria using human genetic material. The human recombinant gelatin is equivalent to the porcine gelatin but may reduce the likelihood of an immune response when injected into an infarct region of a human subject.

Alginate is a linear polysaccharide derived from seaweed and contains mannuronic (M) and guluronic acid (G), presented in both alternating blocks and alternating individual residues. It is possible to use some of the carboxyl groups of the alginate as sites to graft useful cell adhesion ligands, such as collagen, laminin, elastin and other peptide fragments of the ECM matrix, forming an alginate conjugate, because alginate does not have RGD groups for cell retention.

An alginate-gelatin conjugate is valuable because it combines characteristics of alginate with characteristics of gelatin, which include, but are not limited to, RGD sites and immunocompatibility. Characteristics of alginate include rapid, almost instantaneous gelation, and an immune stimulating effect. The alginate-gelatin conjugate can be formed of approximately 1% to 30% and more particularly approximately 10% to 20% gelatin (either porcine or human recombinant) and approximately 80% to 90% alginate. The relatively lower proportion of alginate-gelatin conjugate is used to retain gelation capacity once combined with pure alginate because the alginate carboxyl groups of alginate that cause the gelation may be bound up in the alginate-gelatin conjugate.

Two-component gel systems exhibit different characteristics relative to one another including, but not limited to, pore size, storage modulus and gelation time. The gel system behaves as a sieving media and therefore includes small pores. "Pore size" refers to small, vacuous openings within the gel. "Storage modulus" refers to the strength or the stiffness of the material upon gelation. Storage modulus can be measured by a rheometric instrument. "Gelation time" refers to the kinetics of gelation, the decrease in viscous modulus. Alginate constructs can gel within about 1 second, while fibrin glues can gel between about 5 seconds and about 60 seconds. Self-assembled peptides typically undergo gelation between several minutes to several hours.

In embodiments in which cells are co-injected with the two-component gel system, or mixed with one component before combining the two components, the gel system can exhibit different characteristics relative to one another relating to the cells. Such characteristics can include, but are not limited to, morphology of the cells, cell survivability, encapsulation efficiency and/or cell concentration. "Morphology" refers to the physical structure of the cells. In the case of hMSC, the natural morphology is a flattened spindle-shaped morphology. "Cell survivability" is the amount of time that the cells remain viable within the gel post-injection. "Encapsulation efficiency" refers to the fraction of the initial number of cells in suspension that are entrapped within the gel. "Cell concentration" is the encapsulation efficiency divided by the volume of gel formed.

A characteristic which affects the encapsulation efficiency is the difference in viscosity ($\eta$) of the two components. If the difference in viscosity between the two components of the gelation system is large, then the encapsulation efficiency is high only when cells are in the high viscosity component. However, if the viscosity of each individual component is lowered without compromising the gelation kinetics, the encapsulation efficiency increases dramatically. For a catheter-based delivery system, low viscosity components are very helpful for successful delivery. A successful application of the two components (which are in solution before delivery) can be dependent upon low viscosity of the individual components.

In some embodiments, a bioscaffolding can be formed from a mixture of gel components of different gel systems. For example, a bioscaffolding can be formed by mixing at least two different components (which do not gel upon mixing under standard cath lab process conditions) of at least two different two-component gel systems to form a first mixture, and, by mixing at least two different components (other than the components that make up the first mixture and which do not gel upon mixing under standard cath lab process conditions) of the at least two different two-component gelation systems to form a second mixture. "Gel" generally refers to a semirigid colloidal material formed upon the combination of two different components or two different mixtures. A treatment agent, such as a cell type or a growth factor, can be added to either the first mixture or the second mixture. The first mixture can then be co-injected with the second mixture to form a reinforcement region within the necrotic and/or border zone of the myocardium for treatment thereof. In some embodiments, a bioscaffolding can be formed by mixing at least two different gel components (which do not gel upon mixing under standard cath lab process conditions) to form a first mixture. A treatment agent, such as a cell type or a growth factor, can be added to the first mixture. The first mixture can then be co-injected with a gelation component to form a bioscaffolding on an infarct region for treatment thereof. In some embodiments, the treatment agent can be co-injected with the first mixture or the gel component without first interdispersing the treatment agent within the first mixture or the gelcomponent.

In some embodiments, an alginate construct system can include an alginate-gelatin solution as a first component and a calcium chloride solution as a second component. In some embodiments, human mesenchymal stems cells (hMSC) are suspended in one component of the gelation system. hMSC are thought to be capable of both self renewal and differentiation into bone, cartilage, muscle, tendon and fat. hMSC also give rise to a variety of mature cell types via a step-wise maturation process called mesengenesis. The natural morphology of hMSC is elongated and spindle shaped. The gelatin provides RGA sites for cellular adhesion i.e. adhesion of hMSC. Alginate construct systems exhibit rapid gelling kinetics. When combined, alginate-gelatin and calcium chloride gel to form a bioscaffolding in less than 1 second. The resulting gel has a storage modulus of approximately 1 kiloPascal. In application, cell survivability has been observed up to at least 12 days. Encapsulation efficiency is approximately 99%. However, the small pore size of alginate construct systems, which is from about 2 nm to about 500 nm, can lead to low cell spreadability as observed by the round morphology of the hMSC cells over time. "Cell spreading" refers to the naturally occurring morphology of cells. Advantages of alginate construct systems include, but are not limited to, enhanced immune response (a controlled foreign body response) to effect positive remodeling of the injured myocardium, and immunoprotectivity, by shielding via its small pore size, the encapsulated cells from this enhanced immune response (protected from host immune response), instantaneous gelation kinetics, substantial or complete non-adherence to a needle when injected, and long term cell viability. Furthermore, alginate construct systems degrade slowly (at least 8 weeks in vivo).

Fibrin glue can include fibrinogen (modified or not modified with protein constituents) as a first component and thrombin as a second component. In some embodiments, human mesenchymal stems cells (hMSC) are suspended in one component of the gelation system. Fibrin glue systems exhibit fast gelling kinetics, but not as rapid as alginate construct systems. When combined, fibrinogen and thrombin gel form a bioscaffolding in about 5 seconds to about 10 seconds. The resulting gel has a storage modulus of approximately 3 kiloPascals which is higher than that of alginate construct systems. A higher storage modulus may improve mechanical reinforcement at the infarct region. In application, cell survivability has been observed up to at least 12 days. The pore size of fibrin glue systems is from about 1.5 microns to about 2.5 microns and can lead to high cell spreadability of hMSC cells. That is, hMSC cells have been observed to have an elongate and stellate morphology which is more natural to their endogenous state when compared to the morphology observed in alginate construct systems alone. Advantages of fibrin glue include, but are not limited to, material strength, promotion of angiogenesis, good cytocompatibility (compatible with cell growth), good cell morphology (elongated and stellate) and high cell proliferation in fibrinogen. One further characteristic of fibrin based gels is that they degrade within 2 weeks in vivo.

In some embodiments, a bioscaffolding is formed from mixing components of at least two gel systems. For example, a first component of a first two-component gel and a first component of a second two-component gel can be combined to form a first mixture. A second component of a first two-component gel and a second component of the second two-component gel can be combined to form a second mixture. Cells can be suspended within either the first mixture or the second mixture. When the two mixtures are combined, a bioscaffolding including at least some advantageous characteristics of both gelation systems can be realized. In some embodiments, a bioscaffolding can be formed by mixing at least two different gelation components to form a first mixture. When the first mixture is combined with a gelation salt, a bioscaffolding including at least some advantageous characteristics of the individual components can be realized. It should be appreciated that a number of different combinations of gelation components can be mixed together in different ratios to accentuate various advantageous characteristics of the individual gelation systems. Furthermore, the concentration of the individual components, either singly or combined, can influence certain characteristics of the bioscaffolding, such as viscosity and encapsulation efficiency.

In some embodiments, the bioscaffolding can be formed of an amino or thiol functional poly(ethylene glycol) (PEG) reacted with an oligomer with at least 2 NHS functional groups per molecule. The oligomer may be a multi-arm PEG. In still further embodiments, the bioscaffolding can be formed by other synthetic or naturally occurring polymers such as poly(lactic-co-glycolic acid) (PLGA) or poly(butyl methacrylate) (PMBA) in a solution of dimethyl isosorbide or dimethyl sulfoxide (DMSO) can be used as a single component precipitating material. Injection of this material in the tissue will instantly precipitate the polymer and biocompatible solvent will dissipate into the extracellular fluid.

Alternate gel materials are those that crosslink by exposure to physiological pH. Representatively, the biomaterial may be a mixture of a cationic material such as dimetylaminoethyl dextran and an anionic material such as polystyrene sulfonate. This mixture is a stable solution at low pH as all acid groups are protonated, yet gels when exposed to neutral pH. Alternatively, a gel sensitive to ionic strength may be used. For example, the gel may be Gelsite Aloe derived pectin which, when injected into the myocardium gels within minutes from exposure to blood Calcium.

Treatment Agents

As previously discussed, a treatment agent may be combined with one or more biomaterial components or mixtures of components used to form the bioscaffolding. Representative treatment agents may include, but are not limited to, small molecule drugs, oligonucleotides, peptides and proteins which can inhibit the negative remodeling response, stimulate angiogenesis or regeneration of cardiac tissue.

In one embodiment, the treatment agent may be a drug. Representative drugs include HDL mimetics, anti-inflammatory agents and anti-proliferative agents. Exemplary HDL mimetics include cyclodextrin. Exemplary anti-inflammatory agents include clobetasol, dexamethasone, prednisone, aspirin and cordisone. Exemplary anti-proliferative agents include taxol, everolomus, sirolomus, doxorubicin and other chemotherapeutic agents. In still another embodiment, a treatment agent is an agent that would benefit a damaged blood vessel or an infarcted area. In one sense, a treatment agent is an agent that would benefit a blood vessel or an infarcted area (e.g., tissue) by itself creating new cells or new cell components or trigger a repair mechanism. A treatment agent may also include an agent that may benefit a blood vessel or an infarcted area (e.g., tissue) only with the assistance of another exogenous or endogenous agent. In this aspect, suitable treatment agents may include, but are not limited to, growth factors (e.g., vascular endothelial growth factor (VEGF), fibroblast growth factor (FGF), platelet-derived growth factor (PDGF), insulin-like growth factor (IGF), hepatocyte growth factor (HGF), basic fibroblast growth factor (bFGF), acidic fibroblast growth factor (aFGF), placental growth factor (PlGF), granulocyte colony-stimulating factor (G-CSF)), cellular components, proteins and cytokines. Still further, the treatment agent may include a bioactive agent used to induce regression or slow progress of an atherosclerotic plaque, such as apolipoprotein A1 (Apo A1) or a mutant or mimic form of Apo A1, or a molecule mimicking the cholesterol transporting capacity of ApoA1. The treatment agent may include an agent that inhibits the resorption of bone. Representatively, a suitable agent may be, but is not limited to, bisphosphonate.

In one embodiment, the treatment agent may be a non-living biologic. In one embodiment, the non-living biologic may include scaffolding such as an Extra Cellular Matrix (ECM). Representative non-living biologics may include Urinary Bladder Matrix (UBM), Small Intestinal Submucosa (SIS) and liver derived BioMatrix (LBM).

In another embodiment, the treatment agent may be a living biologic. Representative living biologics include bone marrow stem cells or any subselected fraction thereof, mesenchymal cells, endothelial progenitor cells, skeletal muscle cells, adipose derived stem cells and embryonic stem cells.

In one embodiment, one or more of the above described agents can be encapsulated, suspended, disposed within or loaded into a biodegradable carrier. Examples of biodegradable carriers include, but are not limited to, a liposome, a polymerosome, a micelle, a microsphere, a particle or a gel. Examples of particles include, but are not limited to, microparticles and nanoparticles. Any conventional technique for loading an agent within a carrier may be used.

Delivery Systems

Devices which can be used to deliver modified or combined components of the gelation systems include, but are not limited to, single-needle and dual-needle transvascular wall injection devices. Methods of access to use the minimally invasive (i.e., percutaneous or endoscopic) injection devices include access via the femoral artery or the sub-xiphoid. "Xiphoid" or "xiphoid process" is a pointed cartilage attached to the lower end of the breastbone or sternum, the smallest and lowest division of the sternum. Both methods are known by those skilled in the art.

Figure 5:
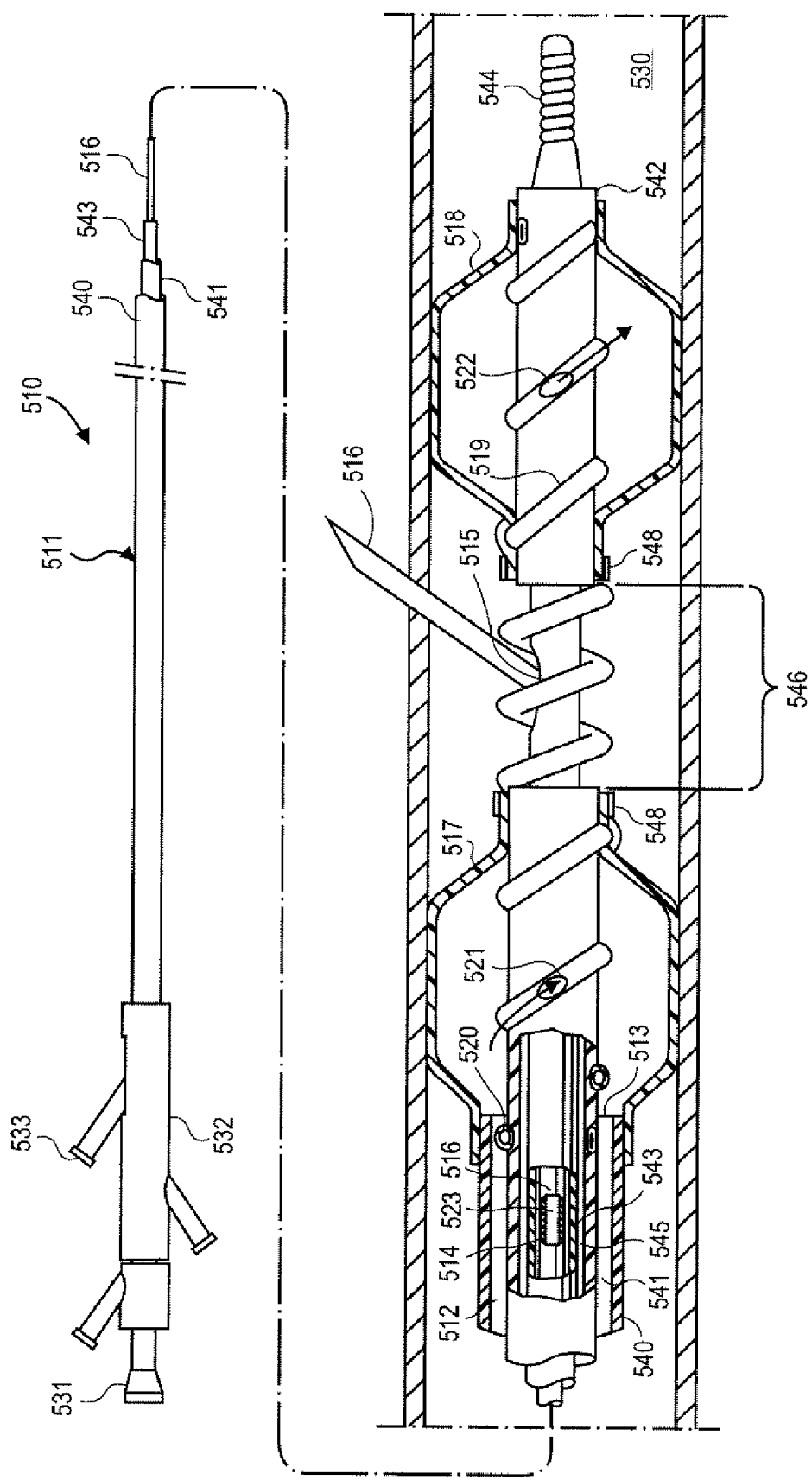
FIG. 5 illustrates an embodiment of a delivery device.

FIG. 5 illustrates an elevational, partially in section, view of a delivery device. Delivery device 510 is a single-needle delivery device. Delivery device 510 is an agent delivery catheter, generally comprising an elongated catheter shaft 511 having a proximal end, a distal end, a distal shaft section and an inflation lumen 512 extending distally from the proximal end of the shaft to a distal end 513 located proximal to a distal end of the catheter. Delivery device 510 includes a needle-through lumen 514 slidably containing a hollow needle 516 therein and at least one needle-through port 515.

Proximal balloon 517 is positioned on the distal shaft section with an inflatable interior located proximal to the needle-through port 515. Distal balloon 518 is positioned on the shaft distal to proximal balloon 517 and has an inflatable interior located distal to the needle-through port 515. Tube 519 defines an inflation bridge lumen 520 extending between the inflatable interiors of balloons 517, 518 from a location proximal to a location distal of needle-through port 515. Proximal balloon 517 is sealingly secured to shaft 511 adjacent to distal end 513 of the inflation lumen 512 such that the proximal balloon inflatable interior is in fluid communication with inflation lumen 512. Inflation bridge tube 519 has a proximal port 521 within the proximal balloon interior and distal port 522 within the distal balloon interior to thereby provide for inflation of distal balloon 518 by placing the distal balloon interior in fluid communication with the proximal balloon interior.

Proximal handle assembly 532 at the proximal end of delivery device 510 is configured for connecting to fluid sources (for flowing biomaterials therethrough, balloon inflation fluid, and/or flushing fluid in the catheter lumens) and provides access to needle-through lumen 514. Proximal handle assembly 532 is typically configured to control needle extension, retraction, and optionally rotational orientation as well. Specifically, a proximal handle 531 at the proximal end of the needle 516 is configured for attaching to a biomaterial source (not shown) to flow biomaterials through lumen 523 of the hollow needle 516 to the piercing distal tip of needle 516. Proximal Y-arm adapter secured to the shaft proximal end has sidearm port 533 configured for connecting an inflation fluid source (not shown) into fluid communication with an inflation lumen 512 of the shaft for inflating balloons 517, 518. The addition sidearm ports may be used for flushing the annular space around needle sheath tubular member 514 and the annular space around needle 516.

Delivery device 510 is configured to be introduced into the patient's vasculature and advanced in a low profile configuration (not shown) in which the balloons 517, 518 are deflated and optionally folded and needle 515 distal end is retracted into the shaft 511 to position port 515 at the desired injection site in the patient's body lumen 530 (e.g., cardiac vessel). Once at the desired injection site, the balloons are inflated and the needle distal end is slidably advanced out port 515 and through a wall of body lumen 530. A biomaterial is delivered from the needle to the tissue (e.g., into the myocardium). The needle distal tip extends radially beyond the outer profile of the inflated balloons, although the catheter is typically configured to allow needle 516 to extend only a set limited distance away from the shaft 511, as for example by providing delivery device 510 with a needle stop member (not shown). FIG. 5 illustrates the balloons inflated against the body lumen wall and needle 516 extending through the wall of body lumen 530. Following an injection, needle 516 is retracted into shaft 511 to allow catheter 510 to be repositioned (typically with balloons 517, 518 in a deflated configuration) or ultimately removed from body lumen 530 at the end of the delivery procedure.

In some embodiments, needle 516 is curved so that when it is advanced into a myocardial tissue it is able to be positioned substantially parallel to the myocardial walls as previously discussed. In other words, the curvature of needle 516 is such that it can pierce through the wall of lumen 530 into the wall of the tissue (e.g. myocardial wall) and run along the tissue wall as opposed to through it.

A depth that needle 516 is advanced into the myocardium is controlled so that the biomaterial is injected into the desired tissue region. Representatively, fluoroscopy, electrocardiograph signals and/or imaging systems (e.g., ultrasonic, magnetic resonance, and optical) may be used to control the needle depth. In still further embodiments, needle 516 may include a device (e.g., thermally conductive heating element) suitable for determining injection depth based on the heat dissipation characteristics of a body tissue such as that described in U.S. Pat. No. 7,762,958 filed on Dec. 19, 2001 and incorporated herein in its entirety.

Shaft 511 includes outer tubular member 540 and inner tubular member 541 extending within the outer tubular member. Shaft 511 further includes extension inner tubular member 542 and needle sheath tubular member 543 disposed within the inner tubular member 541. Inflation lumen 512 is within outer tubular member 540, and more specifically is the annular space between inner tubular member 541 and outer tubular member 540. Inflation lumen 512 is the single inflation lumen of the shaft and the balloons are configured to inflate at the same time (i.e., not independently of each other).

Proximal balloon 517 has a proximal skirt section sealingly secured to the distal end of outer tubular member 540 and a distal skirt section sealingly secured to the distal end of inner tubular member 541. In this aspect, inflation lumen 512 opens into the inflatable interior of proximal balloon 517, placing the inflatable interior of proximal balloon 517 in fluid communication with shaft inflation lumen 512. Distal balloon 518 has a proximal and distal skirt section sealingly secured to extension inner tubular member 542. Needle-through lumen 514 is within needle-sheath tubular member 543 and port 515 is in a sidewall of needle sheath tubular member 543.

Needle sheath tubular member 543 has a closed distal end with a flexible coiled distal tip 544 on the distal end of needle sheath tubular member 543 such that needle-through lumen 514 is a blind (closed ended) lumen. Preferably, lumen 514 is filled with material distal to port 515 to prevent air emboli and/or blood clots from forming in the distal portions of the lumen 514 and to provide a ramp to facilitate the reliable advancement of the distal end of needle 516 out of port 515.

In the embodiment of FIG. 5, delivery device 510 is an over-the-wire (OTW) type catheter in which inner tubular member 541 and extension inner tubular member 542 define a wire lumen 545 therein configured to slidably receive needle sheath tubular member 543 therein. A delivery device catheter of the invention can alternatively have a fixed-wire type shaft design.

Delivery device 510 is advanced to the desired location in body lumen 530 over a guidewire (not shown). Guidewire is then withdrawn from wire lumen 545 and needle-sheath tubular member 543 is slidably advanced therein (with needle 516 retracted into needle-through lumen 514) until needle-through port 515 is positioned between balloons 517, 518 as illustrated in FIG. 5.

Radiopaque markers such as marker bands 548 on the skirt sections of the balloons 517, 518, together with one or more optional additional radiopaque markers (not shown) typically provided on the needle sheath tubular member 543 (e.g., at either end of port 515) facilitate the ability of the physician to slidably position port 515 at the desired location between the two balloons 517, 518 under fluoroscopy. Markers 548 are also useful for positioning the balloons adjacent to the desired treatment site in body lumen 530.

In some embodiments, radiopaque markers (not shown) may be provided on needle 516 to facilitate positioning of needle 516 within the myocardium. In this aspect, the physician is able to determine when needle 516 is advanced through vessel 530 and into a desired region of the myocardium using fluoroscopy.

The proximal end of the extension inner tubular member 542 is distally spaced from the distal end of the inner tubular member 541, thereby forming a longitudinal gap 546 in the shaft, such that the distal balloon 518 and extension inner tubular member 542 are fixedly connected to inner tubular member 541 and proximal balloon 517 only by the inflation bridge tube 519.

Inflation bridge tube 519 has sufficient stiffness to transmit longitudinal forces and torque to ensure that extension inner tubular member 542 is in a force and torque transmitting relationship with inner tubular member 541. Such a configuration facilitates maneuvering of delivery device 510 in the patient's tortuous vasculature. In one embodiment, shaft 511 is reinforced with stiffening members such as small wires configured to improve this torque transmission. Inner tubular member 541, at least along a distal end section of inner tubular member 541 within the inflatable interior of the proximal balloon 517, typically has an inner and outer diameter approximately equal to the inner and outer diameters, respectively, of the extension inner tubular member 542. In some embodiments, especially where the needle sheath outer diameter is substantially larger than the outer diameter of the desired OTW guidewire, the distal portions of extension inner tubular member 542 may be longer than is shown in FIG. 5 and have a distally reduced inner diameter and tapered outer diameter to better fit the OTW guidewire and provide an improved atraumatic distal end during OTW catheter insertion.

Inflation bridge tube 519 provides a fluid path for the inflation fluid to flow from proximal balloon 517 to distal balloon 518 (which would otherwise not be in fluid communication with inflation lumen 512), in order to inflate distal balloon 518. In the embodiment of FIG. 5, only part of the length of the inflation bridge tube 519 extends on an outer surface of the shaft 511. Inflation bridge tube 519 preferably extends helically, to prevent or minimize any disadvantageous stiffness increase in the distal shaft section due to the presence of the inflation bridge tube. The terminology "helically" as used herein should be understood to refer generally to a spiraling configuration as in the shape of a coil, as opposed to an axially aligned member which extends substantially straight (e.g., with no intentionally induced spiraling or curving around the catheter longitudinal axis). In some embodiments, the pitch and/or coil diameter of inflation bridge tube 519 may be adjusted based on its longitudinal position. Inflation bridge tube 519 extends helically from proximal of proximal balloon 517 inflatable interior to distal of distal balloon 518 inflatable interior. In this aspect, inflation bridge tube 519 has a proximal end radially aligned with the proximal skirt section of the proximal balloon and a distal end radially aligned with the distal skirt section of the distal balloon. As a result, a smooth transition in stiffness is provided that resists kinking at the ends of the balloons 517, 518 for improved catheter deliverability.

Once in position such that the user is not applying a pushing or pulling force, the coil turns of tube 519 are configured to atraumatically conform to the curved vascular anatomy at least partially and to retain enough separation between coil turns to allow needle 516 to be extended. Thus, although the coil turns of the helical inflation bridge tube 519 along the shaft gap 546 are configured at least in one embodiment to not disadvantageously longitudinally collapse (by a significant amount) as the catheter is pushed through the vasculature, the longitudinal collapse of the coil turns is expected to some degree, and some degree of collapse is advantageous in that it provides form improved flexibility and deliverability of the catheter. Additionally, the helically extending inflation bridge tube 519 is preferably fanned with sufficiently stiff coil turns to transmit torque and to minimize tightening or unwinding the coiled configuration of tube 519 along shaft gap 546 as the proximal end of the catheter is torqued during maneuvering of the catheter. It should be noted, however, that in the OTW embodiment, it is unlikely that torquing/rotation of the entire catheter is necessary or desirable as the catheter can be positioned simply by pushing it over the OTW guidewire which is already in position. In most fixed wire-type embodiments, the entire catheter must be rotated to cause the catheter's distal tip, which is usually slightly bent, to be rotated to select the desired vascular branches during insertion to the desired site.

Inflation fluid flows into and out of lumen 520 of inflation bridge tube 519 through ports 521, 522 in the sidewall of tube 519 (with arrows indicating the flow of the inflation fluid). The proximal and distal ends of the tube 519 are closed, and sidewall ports 521, 522 may be formed by skiving or grinding a hole in the wall of inflation bridge tube 519, as for example using a rotating cutting or grinding implement, to form a smooth edge that does not pose a significant risk of damaging the balloon wall. Inflation bridge tube 519 is at least partially embedded in the outer surface of inner tubular member 541 and extension inner tubular member 542 in one embodiment, which creates a smooth interface with the shaft 511 along tube 519 that significantly mitigates the risk of damaging the balloon or patient's anatomy.

In the embodiment of FIG. 5, the entire length of the proximal and distal sections of inflation bridge tube 519 on inner tubular member 541 and extension inner tubular member 542 are partially embedded in the outer surface thereof, with the tube extending radially beyond the outer surface of adjacent portions of the shaft by an amount less than an outer diameter of the tube.

In one embodiment, tube 519 is formed separately from the inner tubular members 541, 542. For example, tube 519 may be formed of a NiTi tube that is constrained or wound in the desired coil shape on a grooved mandrel and heated to set the desired shape. Coiled tube 519 may then be embedded in the shaft by forcing the tube (in its helical configuration) over the outer diameter (OD) of inner tubular members 541, 542, and then supporting the inner diameter affected length of members 541, 542 with a low friction mandrel such that tube 519 is deformed while pressing on the OD of the members 541, 542. The assembly is typically subjected to an elevated temperature sufficient to soften the polymeric walls of tubular members 541, 542 and allow the forces of deformed tube 519 to deform the outer walls of members 541, 542 and then the low friction mandrel is removed. In some embodiments, adhesives, such as hot melt adhesives like Primacore®, may be used (for example, applied to in liquid form, placed at in a tubing or cut tubing form, co-extruded on the OD of members 541, 542) on the interface between coil 519 and members 541, 542 prior to heating to bond coil 519 more securely to members 541, 542. In some embodiments, a piece(s) of heat shrink is placed over the assembly prior to heating to aid in pressing tube 519 into members 541, 542 and to aid in forming a smooth outer surface on members 541, 542. After heating/forming, the heat shrink is removed from the assembly. However, a variety of suitable methods of providing the inflation bridge tube 519 and/or lumen 520 can be used, including molding techniques, such as insert or compression molding.

The ends of the tube 519 can be closed by flattening the tube to collapse the lumen 520 at the ends and optionally bonding the collapsed inner surfaces of the tube, or plugging the ends of the tube 519 by for example applying an adhesive to fill the inner diameter at the tube 519 ends. The closed ends of the tube 519 are preferably fully embedded in the wall of the inner tubular members 541, 542, and/or covered (e.g., by the balloon skirt sections) to help ensure that tube 519 ends do not become exposed to the anatomy and cause damage. By increasing the contact area between the inflation bridge tube 519 and inner tubular members 541, 542, embedding the inflation bridge tube 519 improves the overall bond strength and tensile strength of the shaft.

Inflation bridge tube 519 provides support to the needle as the needle is extended from the shaft and through the wall of the patient's body lumen 530. Specifically, when the needle contacts the vessel wall, it creates a reactive load on the catheter body, which can force the catheter shaft away from the vessel wall and make it more difficult to puncture the vessel. The inflation bridge tube 519 limits this disadvantageous instability of the shaft, to facilitate accurate delivery of the agent to a desired injection site.

Figure 6:
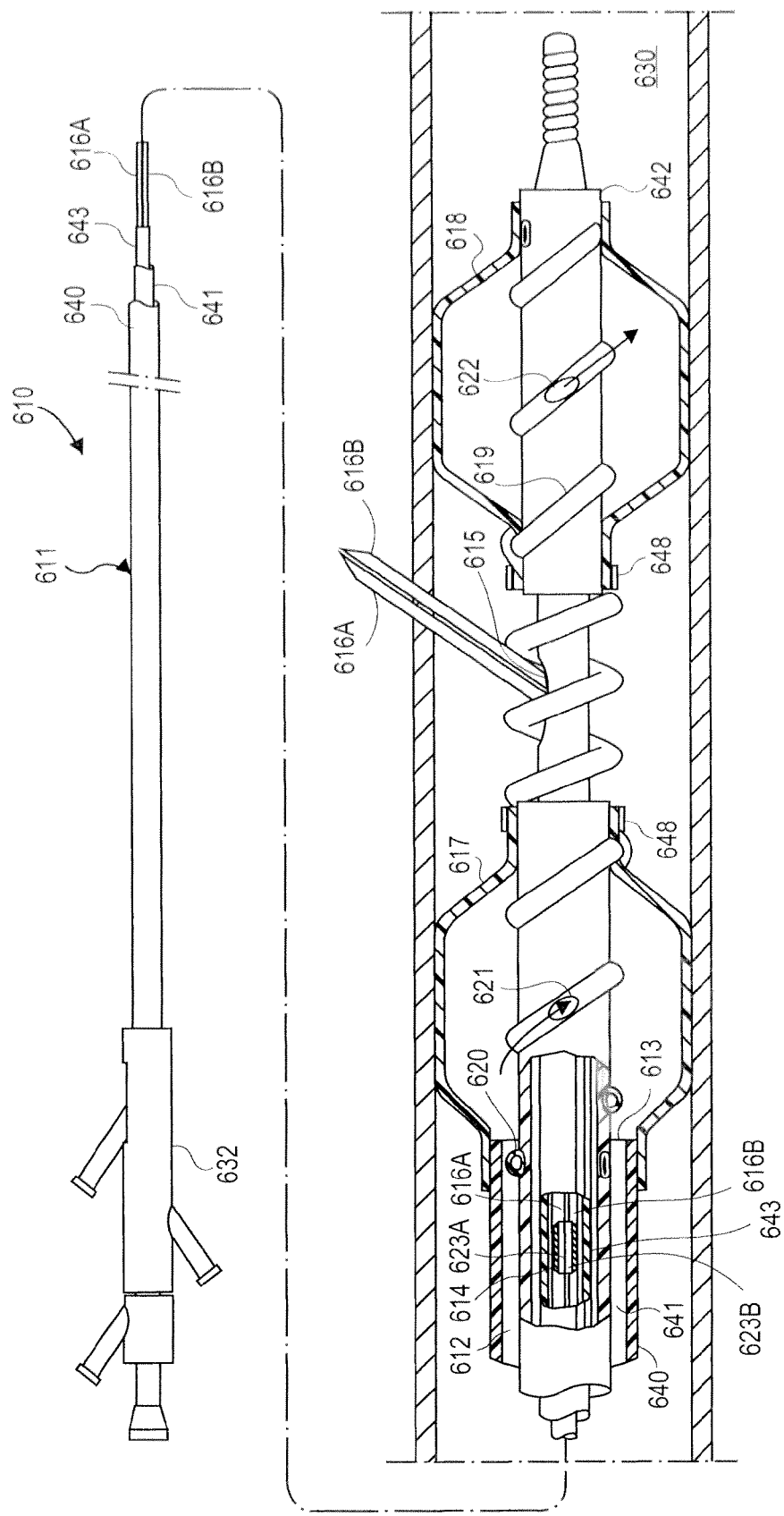
FIG. 6 illustrate an embodiment of a delivery device.

FIG. 6 illustrates an elevational, partially in section, view of a delivery device. Delivery device 610 includes similar components as those disclosed in reference to FIG. 5 except that needle 516 is omitted and replaced with first needle 616a and second needle 616b to facilitate delivery of two-component gel systems. In this aspect, delivery device 610 is an agent delivery catheter, generally comprising an elongated catheter shaft 611 having a proximal end, a distal end, a distal shaft section and an inflation lumen 612 extending distally from the proximal end of the shaft to a distal end 613 located proximal to a distal end of the catheter. Delivery device 610 includes a needle-through lumen 614 slidably containing hollow needle 616a and 616b therein and at least one needle-through port 615.

Proximal balloon 617 is positioned on the distal shaft section with an inflatable interior located proximal to needle-through port 615. Distal balloon 618 is positioned on the shaft distal to proximal balloon 617 and has an inflatable interior located distal to the needle-through port 615. Tube 619 defines an inflation bridge lumen 620 extending between the inflatable interiors of balloons 617, 618 from a location proximal to a location distal of the needle-through port 615. Inflation bridge tube 619 has a proximal port 621 within the proximal balloon interior and distal port 622 within the distal balloon interior to thereby provide for inflation of distal balloon 618 by placing the distal balloon interior in fluid communication with the proximal balloon interior.

Proximal handle assembly 632 at the proximal end of delivery device 610 is configured for connecting to fluid sources (for flowing biomaterials therethrough, balloon inflation fluid, and/or flushing fluid in the catheter lumens) and provides access to needle-through lumen 614. Specifically, a proximal handle at the proximal end of the needles 616a and 616b is configured for attaching to a biomaterial source (not shown) to flow biomaterials through lumens 623a and 623b of the hollow needles 616a and 616b to the piercing distal tip of needles 616a and 616b.

Delivery device 610 is configured to be introduced into the patient's vasculature and advanced in a low profile configuration (not shown). In this aspect, balloons 617, 618 are deflated and optionally folded and needle 615 distal end is retracted into the shaft 611 to position port 615 at the desired injection site in the patient's body lumen 630. Once at the desired injection site, the balloons are inflated and the needle distal end is slidably advanced out port 615, through the body lumen wall and into the myocardial tissue. Biomaterials are delivered from the needle to the tissue (e.g., myocardium). The needle distal tip extends radially beyond the outer profile of the inflated balloons, although the catheter is typically configured to allow needles 616a and 616b to extend only a set limited distance away from the shaft 611, as for example by providing delivery device 610 with a needle stop member (not shown). FIG. 6 illustrates the balloons inflated against the body lumen wall, and needles 616a and 616b partially extended in the wall of body lumen 630. Following an injection, needles 616a and 616b are retracted into shaft 611 to allow catheter 610 to be repositioned (typically with balloons 617, 618 in a deflated configuration) or ultimately removed from body lumen 630 at the end of the delivery procedure.

Needles 616a and 616b are substantially similar to needle 516 of FIG. 5 such that they may be advanced into myocardial tissue parallel to the myocardial walls. In some embodiments, needles 616a and 616b are curved to facilitate positioning of the needles substantially parallel to the myocardial walls as previously discussed.

In still further embodiments, in addition to radiopaque markers 648 on delivery device 610, radiopaque markers (not shown) may be provided on needles 616a and 616b to facilitate positioning of needles 616a and 616b within the myocardium. In this aspect, the physician is able to determine when needles 616a and 616b are advanced through vessel 630 and into a desired region of the myocardium using fluoroscopy.

Shaft 611 includes outer tubular member 640 and inner tubular member 641 extending within the outer tubular member. Shaft 611 further includes extension inner tubular member 642 and needle sheath tubular member 643 disposed within inner tubular member 641. Inflation lumen 612 is within outer tubular member 640, and more specifically is the annular space between inner tubular member 641 and outer tubular member 640. Inflation lumen 612 is the single inflation lumen of the shaft and the balloons are configured to inflate at the same time (i.e., not independently of each other).

Although one type of OTW delivery catheter is described, any other type of delivery device suitable for delivering biomaterials to the myocardium as described herein may be used. Representatively, the delivery device may be a needle injection wire which includes a self-orienting needle positioned within a guide wire. In this aspect, the guide wire may be advanced through a vessel wall and into the myocardium. The needle may then be extended from the guide wire to a maximum desirable length which is sufficient to deposit a biomaterial within a necrotic zone, border zone and/or remote zone of the myocardium. In still further embodiments, the delivery device may be a needle injection catheter having an imaging device coupled thereto such as that disclosed in U.S. Pat. No. 6,702,744 filed on Nov. 30, 2001 and incorporated herein in its entirety In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method comprising:
    introducing a delivery device through a vessel wall to a treatment site within a myocardium, the treatment site comprising a necrotic tissue and a border region tissue adjacent to the necrotic tissue; and
    delivering a biomaterial to the treatment site as the delivery device is withdrawn from the treatment site to form a plurality of reinforcement regions within the myocardium,
    wherein each of the reinforcement regions comprise a first end terminating within the necrotic tissue and a second end terminating within the border region tissue such that the reinforcement regions transverse the necrotic tissue and the border region tissue and suture the necrotic tissue to the border region tissue, and
    wherein the plurality of reinforcement regions are spaced apart around a periphery, of the necrotic tissue.

2. The method of claim 1 wherein introducing comprises positioning the delivery device substantially parallel to a wall of the myocardium.

3. The method of claim 1 wherein the biomaterial comprises a single-component gel system or a two-component gel system.

4. The method of claim 3 wherein the single-component gel system is selected from the group consisting of a biocompatible acrylate agent, a self-assembled peptide, a silk-elastin block co-polymer and sodium hyaluronate.

5. The method of claim 3 wherein the two-component gel system is selected from the group consisting of an alginate construct system, a fibrin glue system and a self-assembled peptide system.

6. The method of claim 1 further comprising:
delivering a treatment agent to the treatment site.

7. The method of claim 6 wherein the treatment agents is selected from the group consisting of a growth factor, a cellular component, a protein and a cytokine.

8. The method of claim 6 wherein the treatment agent is a drug selected from the group consisting of an HDL mimetic, an anti-inflammatory and an anti-proliferative.

9. The method of claim 6 wherein the treatment agent is a non-living biologic selected from the group consisting of extra cellular matrix, urinary bladder matrix, small intestinal submucosa and liver derived biomatrix.

10. The method of claim 6 wherein the treatment agent is a living biologic selected from the group consisting of bone marrow stem cells, mesenchymal cells and endothelial progenitor cells.

11. The method of claim 1 wherein a plurality of treatment sites are within the myocardium and the plurality of reinforcement regions are formed within each of the plurality of treatment sites.

12. The method of claim 1 wherein the delivery device is one of a single-lumen delivery device or a dual-lumen delivery device.

13. A method comprising:
introducing a delivery device through a vessel wall to a region within a myocardium such that the delivery device is positioned within the myocardium substantially parallel to a wall of the myocardium; and
delivering a biomaterial into a plurality of separately defined spaces formed within the region by the delivery device to form a plurality of separately defined reinforcement regions within the myocardium, wherein the plurality of reinforcement regions comprise a first end terminating within a necrotic tissue and a second end terminating within a border region tissue adjacent the necrotic tissue such that the reinforcement regions transverse the necrotic tissue and the border tissue and suture the necrotic tissue to the border tissue.

14. The method of claim 13 wherein the biomaterial comprises a single-component or a two-component gel system.

15. The method of claim 13 further comprising:
delivering a treatment agent into the space.

16. The method of claim 13 wherein the delivery device is one of a single-lumen delivery device or a dual-lumen delivery device.

17. A method comprising:
forming a first reinforcement region within a necrotic tissue region of a myocardium by delivering a biomaterial into a first space formed across the necrotic tissue region and an adjacent border tissue region by a delivery device withdrawn therefrom, wherein the first reinforcement region comprises a first end terminating within the necrotic tissue region and a second end terminating within the border tissue region; and
forming a second reinforcement region within the necrotic tissue region by delivering the biomaterial into a second space formed across the necrotic tissue region and the adjacent border tissue region by the delivery device, wherein the second reinforcement region is separate from the first reinforcement region and comprises a first end terminating within the necrotic tissue region and a second end terminating within the border tissue region.

18. The method of claim 17 wherein the delivery device is introduced through a vessel wall to the myocardium in a direction substantially parallel to a wall of a myocardium.

19. The method of claim 17 wherein the biomaterial comprises a single-component or a two-component gel system.

20. The method of claim 17 further comprising:
delivering a treatment agent into the space.

21. The method of claim 17 wherein the delivery device is one of a single-lumen delivery device or a dual-lumen delivery device.

* * * * *